US009916612B2

(12) United States Patent
Morris et al.

(10) Patent No.: US 9,916,612 B2
(45) Date of Patent: Mar. 13, 2018

(54) USER-STATE MEDIATED PRODUCT SELECTION

(71) Applicant: Intel Corporation, Santa Clara, CA (US)

(72) Inventors: Margaret E. Morris, Portland, OR (US); Susan A. Faulkner, Hillsboro, OR (US)

(73) Assignee: Intel Corporation, Santa Clara, CA (US)

( * ) Notice: Subject to any disclaimer, the term of this patent is extended or adjusted under 35 U.S.C. 154(b) by 75 days.

(21) Appl. No.: 14/294,428

(22) Filed: Jun. 3, 2014

(65) Prior Publication Data

US 2015/0348162 A1 Dec. 3, 2015

(51) Int. Cl.
*G06Q 30/00* (2012.01)
*G06Q 30/06* (2012.01)
(Continued)

(52) U.S. Cl.
CPC ....... *G06Q 30/0631* (2013.01); *A61B 5/0077* (2013.01); *A61B 5/165* (2013.01); *G06K 9/00302* (2013.01); *G06Q 30/0269* (2013.01); *G06Q 30/0281* (2013.01); *G06Q 30/0282* (2013.01); *G06Q 50/01* (2013.01);
(Continued)

(58) Field of Classification Search
CPC ............... G06Q 30/0282; G06Q 20/18; G06Q 30/0631; G06Q 30/0269; G06Q 30/0281; G06Q 30/02; G06Q 50/01; G06Q 50/22; G07F 7/00; G07F 9/00; H04N 7/18; G06K 9/00302; A61B 5/0077; A61B 5/165;
(Continued)

(56) References Cited

U.S. PATENT DOCUMENTS 8,041,801 B2 * 10/2011 Nakamura ........ G06F 17/30867
340/321
8,321,299 B2 * 11/2012 Smith .................... G06Q 30/02
705/26.1
(Continued)

FOREIGN PATENT DOCUMENTS

JP 2002298215 A 10/2002
KR 20090129264 A 12/2009
(Continued)

OTHER PUBLICATIONS

Intelligent Menu Ordering System. Catalano, Anthony B. Aug. 15, 2010 (Aug. 15, 2010). Accessed via ProQuest [https://dialog.proquest.com/professional/docview/743346325?accountid=142257]. (Year: 2010).*

(Continued)

*Primary Examiner* — Resha Desai
*Assistant Examiner* — Allison G Wood
(74) *Attorney, Agent, or Firm* — Jordan IP Law, LLC

(57) ABSTRACT

Systems and methods may provide purchasing suggestions to consumers based on the emotional, financial, social or physiological state of the consumer. The state of a consumer is based on data that may be collected from a variety of sources, including image data and biosensor data collected at the point of sale, as well as data accessible via smart phone or stored elsewhere. The systems and methods may be practiced in the context of a vending machine, bricks-and-mortar store, on-line store, or other venue.

25 Claims, 4 Drawing Sheets

(51) Int. Cl.
| | |
|---|---|
| *H04N 7/18* | (2006.01) |
| *G06K 9/00* | (2006.01) |
| *G07F 9/00* | (2006.01) |
| *G06Q 30/02* | (2012.01) |
| *G06Q 50/00* | (2012.01) |
| *A61B 5/00* | (2006.01) |
| *A61B 5/16* | (2006.01) |
| *G06Q 50/22* | (2018.01) |
| *A61B 5/024* | (2006.01) |
| *A61B 5/145* | (2006.01) |

(52) U.S. Cl.
CPC ............... *G07F 9/00* (2013.01); *H04N 7/18* (2013.01); *A61B 5/024* (2013.01); *A61B 5/14507* (2013.01); *A61B 5/14532* (2013.01); *A61B 5/14542* (2013.01); *G06Q 30/02* (2013.01); *G06Q 50/22* (2013.01)

(58) Field of Classification Search
CPC . A61B 5/024; A61B 5/14507; A61B 5/14532; A61B 5/14542
USPC ........... 705/26.1–27.2, 14.66, 26.7, 346, 347
See application file for complete search history.

(56) References Cited

U.S. PATENT DOCUMENTS

| | | | |
|---|---|---|---|
| 8,340,815 B2 | 12/2012 | Peters et al. | |
| 2005/0211768 A1 | 9/2005 | Stillman | |
| 2007/0093934 A1* | 4/2007 | Garneau, III | G06F 19/3462 700/236 |
| 2009/0245603 A1* | 10/2009 | Koruga | A45D 44/00 382/128 |
| 2009/0276368 A1* | 11/2009 | Martin | G06Q 40/06 705/36 R |
| 2012/0265636 A1 | 10/2012 | Moeggenberg | |
| 2012/0265637 A1* | 10/2012 | Moeggenberg | G06Q 30/06 705/26.8 |
| 2012/0290508 A1* | 11/2012 | Bist | G06F 17/30035 706/10 |
| 2013/0046637 A1 | 2/2013 | Slutsky et al. | |
| 2013/0054016 A1 | 2/2013 | Canter et al. | |
| 2013/0325641 A1 | 12/2013 | Brown et al. | |
| 2014/0147018 A1 | 5/2014 | Argue et al. | |
| 2014/0172627 A1* | 6/2014 | Levy | G06Q 30/02 705/26.7 |
| 2014/0179231 A1* | 6/2014 | Charania | G07F 11/002 455/41.2 |
| 2014/0214480 A1* | 7/2014 | Jamal | G06Q 30/0201 705/7.29 |
| 2014/0365336 A1* | 12/2014 | Hurewitz | G06Q 30/0643 705/26.62 |

FOREIGN PATENT DOCUMENTS

| | | |
|---|---|---|
| KR | 20100078507 A | 7/2010 |
| WO | 2015/187725 A2 | 12/2015 |

OTHER PUBLICATIONS

Doyle, Maria, Google Contacts Will Help Diabetics Monitor Blood Sugar Via Tears, Forbes, [retrieved on Mar. 21, 2014] from the Internet: <URL: http//www.forbes.com/sites/ptc/2014/02/12/google-contacts-will-help-diabetics-monitor-blood-sugar-via-tears/>, available prior to Jun. 3, 2014, 3 pages.
Ekman, Paul et al., The Symmetry of Emotional and Deliberate Facial Actions, Psychophysiology, vol. 18 No. 2, 1981, 6 pages.
Russell, James, A Circumplex Model of Affect, Journal of Personality and Social Psychology, vol. 39, No. 6, pp. 1161-1178, 1980, 18 pages.
International Search Report for International Application No. PCT/US2015/033824, dated Aug. 31, 2015, 3 pages.
Written Opinion of the International Search Report for International Application No. PCT/US2015/033824, dated Aug. 31, 2015, 10 pages.
Extended European Search Report for EP Application No. 15165811.9, dated Aug. 13, 2015, 6 pages.

* cited by examiner

USER-STATE MEDIATED PRODUCT SELECTION

BACKGROUND

Consumer decisions regarding the purchase of goods are often impulsively made without benefit of a full analysis of the advantages and disadvantages of the purchasing decisions. This holds true in a variety of contexts. In some settings, such as a traditional brick-and-mortar store, sales staff may be available to help guide the consumer in his purchase. However, even where there is a sales person or other human intermediary about to help guide the selection, insufficient information may lead to a poor choice for that particular consumer. Moreover, the human intermediary (e.g., a friend or a sales clerk), may be motivated by concerns that do not place the interests of the consumer interests first. For example, a sales clerk working on commission may be more motivated by profit than by a desire to enhance the consumer's well-being. Even when sales staff mean well, they often simply do not have sufficient knowledge concerning the customer.

The economics of selling small, inexpensive items may preclude hiring any specialized sales staff, and in other contexts there may be no one on hand at all to aid the consumer. One example of this scenario arises in the context of consumers purchasing items from vending machines. Typically, a consumer approaches a vending machine, observes what is available, and makes a selection based on his preferences at that moment. Other information that the consumer might bring to bear on that selection, such as his weight, blood sugar levels, mood and long term goals/values are lost in the impulse of the brief moment, possibly to the detriment of the consumer, and possibly representing a lost opportunity to provide the consumer with a profitable item that, were she to give the matter her full attention, would result in a better decision and enhanced good will for the vendor.

BRIEF DESCRIPTION OF THE DRAWINGS

The various advantages of the embodiments will become apparent to one skilled in the art by reading the following specification and appended claims, and by referencing the following drawings, in which:

DETAILED DESCRIPTION

As used herein, the term "product" may refer to any item or service that a consumer may purchase. The term "dispenser" may refer to any mechanism that dispenses a product to a consumer. This mechanism may be all or part of a vending machine, or it may be physically removed from the point of purchase (e.g., a package delivery service).

A vending machine may be taken as an example of a context of consumer purchasing behavior in which the process of product selection begins with the consumer, typically in response to a basic need such as thirst or hunger felt in proximity to the vending machine. Embodiments disclosed herein provide the consumer with purchasing suggestions that may be more aligned with her interests since they follow a dispassionate machine-driven analysis of the consumer's state, as shall be further explained below. Humans are prone to temporal discounting and a tendency to seek immediate gratification, but analysis techniques discussed herein may proceed in terms of long term goals. More particularly, that analysis, conveyed in the form of suggestions, may be made available to the consumer before she has made any purchasing decision.

As used herein, the "state" of a consumer may refer to any or all of the consumer's physical health, frame of mind, physiology, mood, overall happiness, social condition, economic well-being, calendar limitations, or any other set of considerations that an idealized consumer, fully considering every purchase to the fullest and armed with expert opinion to help him, might take into consideration before making a purchase.

Figure 1:
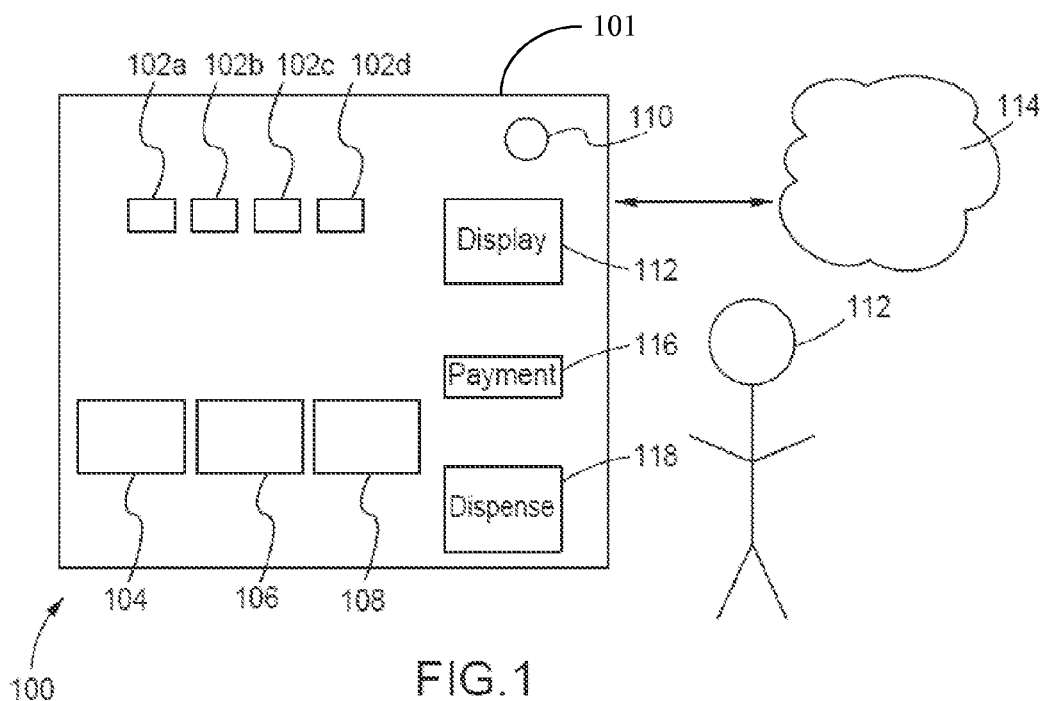
FIG. 1 is a schematic view of an example of a system according to an embodiment.

Turning now to the drawings, an example of a product dispenser according to an embodiment is shown in FIG. 1. While this embodiment is initially developed in terms of use with a vending machine, in other embodiments the system may be adapted to be used in other venues and/or settings, including a brick-and-mortar store and an online store.

An illustrated system 100 includes a vending machine 101 that may be provided with a number of selection buttons 102a-102d, indicative of products available for purchase. Also provided in this embodiment is a biometric sensor port 104 for optional use by a consumer 112 prior to making a purchase. Biometric sensors, which may be touch sensors, may detect a variety of characteristics indicative of a person's state, including pulse rate, blood oxygen levels through pulse oximetry, body temperature, blood sugar levels, and galvanic skin response (GSR). The consumer 112 may further communicate with the system via other modes, such as near field communications (NFC) through port 106, or via Wi-Fi (Wireless Fidelity, e.g., Institute of Electrical and Electronics Engineers/IEEE 802.11-2007, Wireless Local Area Network/LAN Medium Access Control (MAC) and Physical Layer (PHY) Specifications), Bluetooth (e.g., IEEE 802.15.1-2005, Wireless Personal Area Networks) or other communications protocol via a port 108. Additional sensors, which may include sensors worn on the consumer 112, may communicate with the system 100 via any of these wireless technologies, and may provide additional information. For example, so-called "smart" contact lenses may determine blood sugar levels by analyzing tears and transmit this information remotely to the vending machine 101. A camera 110 may also be present to provide images of the consumer 112. The vending machine 101 may have a display 112, a payment block 116, and a dispensing area 118 where the consumer 112 retrieves the results of the purchase. The vending machine 101 may be connected to a computer network such as a cloud 114 (e.g., cloud computing infrastructure).

Figure 2:
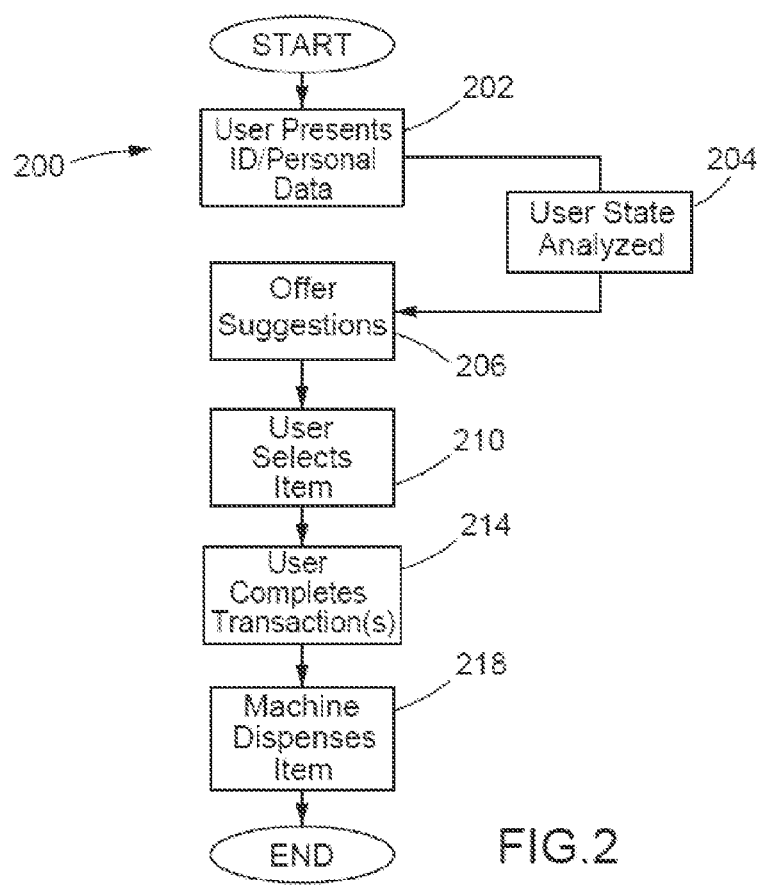
FIG. 2 is a flowchart of an example of a method of providing guidance to a consumer according to an embodiment.

Turning now to FIG. 2, a flowchart of one example of a method 200 according to an embodiment is shown. At block 202 the consumer presents some identifying information or personal data from which his state may be determined. This information may be analyzed at block 204 and then purchasing suggestions are offered at illustrated block 206 based on that analysis. The consumer makes his selection at block 210, which may or may not correspond to one of the suggested selections, pays for his selection at block 214, and at illustrated block 218 the machine dispenses the item the consumer has selected.

Figure 3:
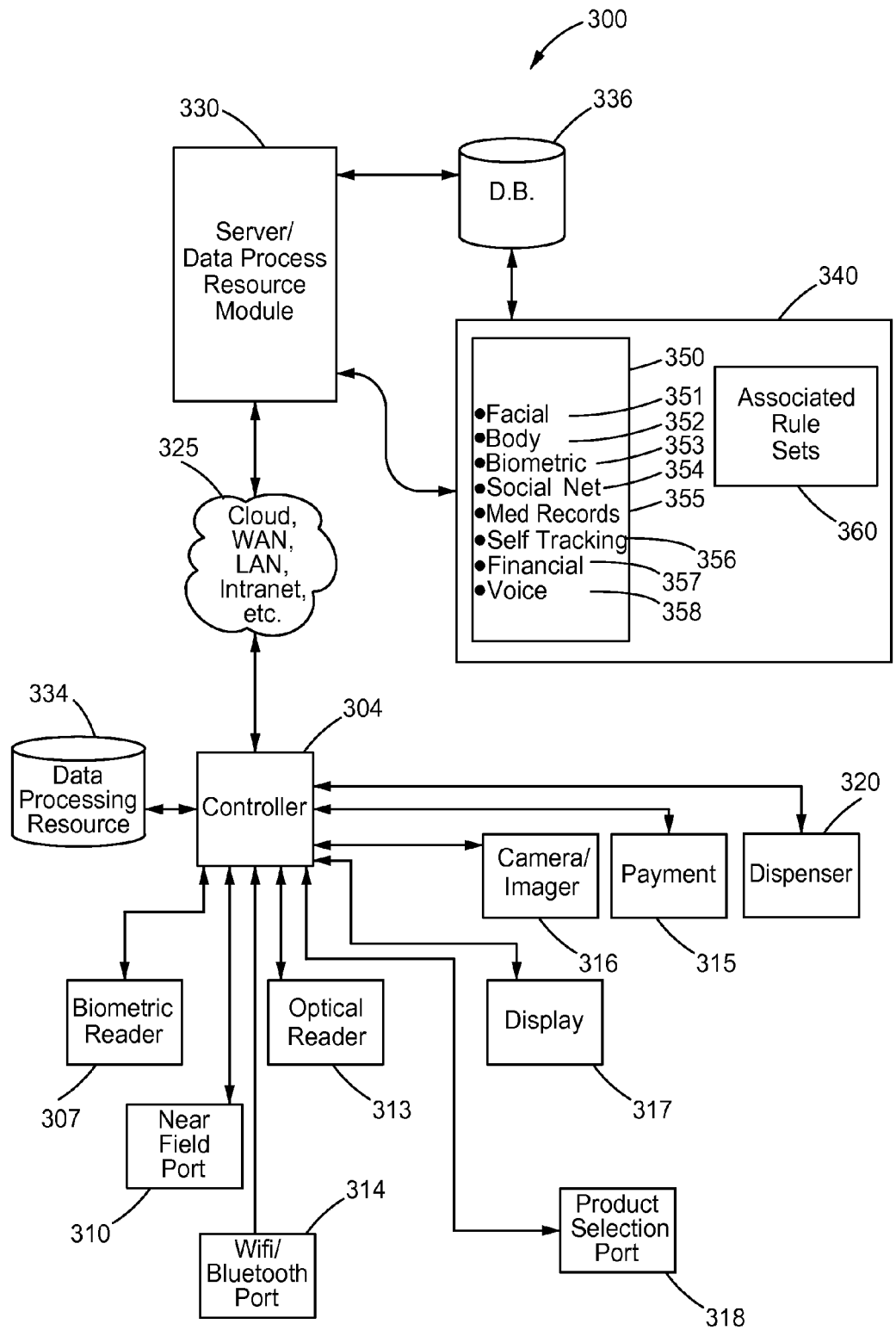
FIG. 3 is a block diagram of an example of a system that includes a product dispenser according to an embodiment.

A more detailed view of a system according to an embodiment is presented in FIG. 3. In this embodiment, a system 300 may operate in a networked computer environment that includes at least one network in communication with a product dispenser. In the example depicted in FIG. 3, a dispenser 320, which may dispense products, is coupled to a communications network 325, which in some embodiments may be a data network. In this example, the dispenser 320, which may further be a vending machine such as the vending machine 101 (FIG. 1), may interface with a consumer, customer, or other consumer. The example product dispenser 320 may be a client-type device, and it may be a computer or processor-based device capable of communicating with the communications network 325 via one or more signals, such as wireless frequency signals or direct wired communication signals.

The system may include a processor or controller 304 to which a variety of devices are connected, including various input ports for obtaining information from which the system may judge the consumer's state. A biometric reader 307 provided with one or more of any of a variety of biometric sensors may be provided for use by a consumer. These biometric sensors may be of any known type, including a cuff that measures blood pressure, or a touch sensor that measures pulse rate, blood oxygenation levels, body temperature, or electrical activity (e.g., GSR, as noted above). In addition to providing information concerning the physiological state of the consumer, a biometric sensor may also be used to verify the consumer's identity. For example, a fingerprint reader may be integrated into the biometric sensor to read the consumer's fingerprints, which may then be used to determine that consumer's identity and to access any information concerning the consumer that has been stored on a server that is available to the system 300.

As a practical matter, the kind of information that is gathered here in a commercial setting may be limited by the willingness of the individual consumer to spend time at the biometric reader 307. Hence, it is useful to provide the consumer with other, possibly more expeditious ways of providing such information as she may be comfortable sharing with the system. For example, another way that information may be transmitted to the system may be by use of a smart card onto which such information has been encoded for reading at a near field communications port 310. The types of information that may be encoded onto a smart card is expansive, and may include any portion of the consumer's medical history that the consumer may choose to make available to the system. Similarly, a smart card may be encoded with any financial information, access permissions for social media, personal calendar, as well as such social or work information that the consumer may wish to make available. Alternatively, an optical reader 313 may be used to read in such information coded in optical form onto a card. For many consumers, the most convenient form of transmitting information to the system will be through the built-in data storage and communications systems capabilities offered by their mobile phones (especially so-called smart phones) and computer tablets. These may be configured to communicate with the system 300 via a Wi-Fi or Bluetooth connection at port 314.

Alternatively, a consumer may simply enter an identifying code as she would when using an automated bank teller. Once the identity of the consumer is established, access may be had to records stored elsewhere that the consumer may have provided for use by the system 300.

Payment, where such is required, may be made through any known payment port at port 315, including cash, debit, or credit card systems. Payment may also be made by a mobile phone or through an account with an employer.

A camera 316 may be provided at a position suitable for capturing images of the consumer, for reasons as shall be further developed below. The camera 316 may be a digital camera standing alone or it may be part of a general imaging system having an imager. It is contemplated that either or both of images of the consumer's face as well as a broader image taken of the consumer's body may be acquired at this stage. Also connected to the illustrated controller 304 are a display 317 and a dispenser 320. In one embodiment, the dispenser 320 is an electromechanical mechanism of a vending machine that dispenses product. In another embodiment, the dispenser 320 may be the fulfillment software used with a web-based store, and in another it may refer to the warehouse and related structures and mechanisms from which merchandise is obtained for delivery to a customer.

The controller 304 conveys data collected on the aforementioned ports 307, 310, 313, 314, and camera 316 through a communications network 325 to a server/data processing resource 330. This data network may be in the form of a LAN, WAN, internet, the cloud, etc. The illustrated server/data processing resource 330 is connected to a database (D.B.) 336 and suggestion logic unit (SLU) 340. In some embodiments, the SLU 340 may be bundled with the resource/data processing resource 330, and in others it may be remotely located from it. Moreover, while these elements are indicated as being linked to the controller 304 through the illustrated communications network 325, they may be all or partly bundled together in a data processing resource 334 that is local to the point of use by a consumer.

Purchasing decisions are often mediated by the emotional state of the consumer, and often detrimentally so. Psychology research has shown that low moods are associated with difficulty negotiating, indulgence in comfort eating and lapsing on health goals. The decision may also be driven by an incomplete understanding on the part of the consumer of his or her over-all state. In one example according to an embodiment, the consumer's state may be seen to be made up of a number of components:

a. emotional state, e.g., is the consumer happy, sad or stressed;
b. physiological state, including the consumer's health issues and recent health behaviors such as exercise and sleep;
c. social state and connectivity;
d. financial state;
e. calendar state, which relates to constraints on the consumer that are calendar driven, such as the need to catch an early morning flight the next day.

These states are not necessarily mutually exclusive. For example, a consumer's social state, including the depth of his personal connections to others, may be bound to his emotional state; a consumer's financial health may be reflected in his emotional state, and so forth. The determination of these states collectively provides a determination of the overall consumer state, and it may be used to guide the consumer towards making purchasing decisions that are in his better interest than may typically be the case with decisions arrived at through less systematic or no deliberation. Additionally, such state information may be utilized by merchants to help enhance profits by selling items that the consumer might otherwise not consider.

The determination of the consumer's state is carried out within the SLU 340, which uses the data provided by the various inputs to the controller or otherwise available to generate suggestions to the consumer that are reflective of the consumer's state and the context in which the system is used. For example, in the example of the system 300 being used with a vending machine, the system 300 may provide the consumer with suggestions via the display 317. If the system is accessed in a store, it may offer suggestions relevant to a retail store setting. Where the system 300 is used in the context of an on-line store, the system 300 may offer suggestions appropriate to that setting.

Within the illustrated SLU 340 are a characterization module 350 and a rule module 360. The characterization module 350 may contain a set of analytical modules responsible for analyzing specific types of data that are then used to provide a characterization of the consumer's state. In the example depicted, these analytical modules include a facial analysis module 351, body morphology analysis module 352, biometrics analysis module 353, social network analysis module 354, medical records analysis module 355, self-tracking analysis module 356, financial analysis module 357, and voice analysis module 358. This listing is not intended to be restrictive or exhaustive, and in other embodiments more or fewer analytical modules may be used.

Each of these modules, either working individually or, depending on the specific implementation, in concert with other modules, may provide information with which the characterization module 350 may characterize the consumer's state. How that state information is used to determine purchasing suggestions to be offered to the consumer may be determined by corresponding rule sets in the rule module 360. There may be one rule set for each module or one large rule set, and rule sets may vary with the setting of the consumer purchase or goal of the system. For example, rule sets may be drafted to enhance the consumer's state and/or to maximize merchant profit. Each of the analytical modules within the characterization module 350 will now be discussed in turn.

One aspect of consumer state is his emotional state, and several of the modules may conduct analysis that enable a determination of the consumer's emotional state. Studies of human psychology have long been mined by marketing specialists and psychologists alike to determine how purchasing decisions and emotional state vary with one another. A consumer's emotional state may impact his purchasing decision process, and the results of that process—the decision to buy something—may in turn affect both his emotional and physical state. Embodiments disclosed herein permit the use of that knowledge in real time to the benefit of the consumer. By correctly characterizing the consumer's emotional state, suggestions may be made to help change that state from one that is relatively bad (e.g., being sad) to one that is better (e.g., feeling happy). If the user is in a negative emotional state, the system 300 may help her stick with her "policies" set according to long term goals (e.g., as derived from health applications on a smart phone or tablet). The system 300 may provide suggestions to the consumer to resist impulse purchases in this state, and instead encourage the consumer to select from one or more suggestions that are consistent with the consumer's previously set policies, which may be incorporated into the rule sets of the rule module 360.

One pathway to ascertaining and characterizing a consumer's emotional state is through consideration of her facial expression. Specifically, an image of the consumer's face may be taken and analyzed, wherein such analysis may begin with the facial analysis module 351. In this regard, a growing number of software packages exist that identify and analyze facial expressions. One system is based on the Facial Action Coding System (FACS) and the work of Paul Ekman, Wallace V. Friesen, and Joseph C. Hager. Additionally, the Affdex® facial recognition and analysis software developed and sold by the Affectiva Company as well as other software for this purpose are now widely available. These solutions may be used to conduct the automated analysis of a consumer's face to determine the consumer's emotional state.

Briefly, some of these solutions operate by coding a facial expression with identifying key points on a person's face and analyzing their relative positions with respect to one another. This information may be interpreted by reference to a database of similarly analyzed facial expressions that psychologists and other researchers have determined to be associated with a particular emotional state to a statistically significant degree. In one approach, a facial expression that is similar to one that has been determined to be "happy" or "excited" may be so characterized by the module. Another facial expression that is similar to one that looks "sad" or "worried" may be characterized as such by the facial analysis module 351.

As facial expression may be tied very closely to emotional state, the facial analysis module 351 may itself be used to determine the consumer's emotional state. For example, if the facial expression is read as "happy," then the characterization module 350 may automatically characterize the consumer as "happy." If, on the other hand, the facial analysis module 351 interprets the facial expression as one of sadness, the characterization module 350 may directly conclude that the emotional state of the consumer is one of sadness.

Another model of emotion that may be used with the analytical modules here is the Circumplex Model of Emotion (CME) developed by James A. Russell and others. This model graphically characterizes emotions on a two dimensional Cartesian plot, in which the horizontal axis corresponds to a valence value of the emotion and the vertical axis corresponds to its arousal value. In this model, valence corresponds to negativity or positivity of an experience, and arousal pertains to the degree of intensity of response. Winning a substantial prize in a lottery would then have a high valence and a high arousal. Denting one's car in a traffic accident would be expected to have a negative valence and a high arousal and so forth. The CME model plots emotions onto such graphs, and facial expressions may be mapped onto emotional states that the CME model characterizes as described above. Alternatively, a user's facial expression may be characterized according to 6-8 distinct emotions. These emotions may be used on their own as a terminal classification of emotional state, or they may be further plotted onto the CME model. There are also other models of emotional state, such as the Vector Model, the Positive activation-Negative Activation Model, etc., and any of these may be used in the implementation of embodiments.

Whichever the model used in the facial analysis module 351, the facial expression of a consumer may be analyzed to determine the consumer's emotional state as per that model. This determination may, standing by itself, constitute the emotional state determination made by the characterization module 350. An associated rule set within the rule module 360 may then be used to determine suggestions for purchases that may be conveyed to the consumer via the display 317. For example, the vending machine may be used in a movie theater to dispense tickets to movies. The rule module

360 may suggest, for example, that a consumer who the facial analysis module 351 has determined to be sad should purchase a ticket to see a comedy (e.g., based on the rule set). In another example, the rule module 360 may suggest some other entertainment that has been adjudged to be suitable for viewing by that consumer, based on the information at hand, which may include the consumer's age, gender, and such prior movie selections as may be stored in the database 336.

The characterization of the consumer's emotional state based on facial expression as determined in facial analysis module 351 may be but one element of a deeper analysis of emotional state, augmented by additional modules. For example, the body morphology analysis module 352 may analyze the posture of the consumer by analyzing additional images provided by the camera 316, as posture itself may be reflective of emotional state.

Another approach to characterizing a consumer's emotional state utilizes self-reported characterizations such as may be provided through an application on a smart phone or tablet. Applications may track these self-reported indications of mood or state and communicate them to the system via any known communications mode, such as through the cloud, near field communications, Wi-Fi etc. These communications may be analyzed at the self-reporting analysis module 356 to determine the consumer's emotional or other state. Additionally, elements of mood, such as arousal, may also be inferred from data provided concerning the consumer's GSR, pulse rate, and blood oxygen levels, which may be analyzed by the biometrics analysis module 353. According to another embodiment, a voice analysis module 358 may be employed to ascertain the consumer's mood or emotional state. The characterization module 350 may determine the consumer's emotional state by utilizing combination of the modules 350-358.

Other aspects of consumer state pertain to physical health, and this may have an important role to play in generating suggestions for food and drink. The biometrics analysis module 353, depending on the particular sensors employed at the biometric reader 307, may provide information on pulse rate, blood oxygen levels, blood sugar levels which may be gleamed from analysis of tears, as noted above and other factors which may relate to health. Either directly or in concert with additional analysis provided by the other modules (e.g., the medical records analysis module 355 may mine medical records to identify health issues), the consumer's physiological state may be characterized, and an associated rule set within the rule module 360 may then generate one or more suggestions. For example, if the consumer is seen to have a high body mass index (this may be determined by the body morphology analysis module 352 by analyzing images taken by camera 316 of the consumer's body) and poor blood oxygen levels, then the SLU 340 may suggest an apple over a candy bar, or a bottle of water over a 32 ounce soft drink. If the consumer chooses not to use the biometric reader 307 but has provided the system with access to his medical records in whole or in part, these may be analyzed by the medical records analysis module 355. For example, if a consumer is indicated as being diabetic, the corresponding rule may be "do not drink sugar-laden water."

In different settings, different rule sets may offer different suggestions. There are many other situations where a commercial transaction may benefit from consideration of the consumer's health, such as in ordering meals at a restaurant. In this setting, instead of interfacing with a vending machine, the consumer may use the camera and biosensor that may be provided with his smart phone, and receive dietary suggestions specific to the restaurant she is in. In this context, a restaurant may be identified by its global positioning system (GPS) coordinates and the associated rule set within rule module 360 may relate to items on its menu. In one embodiment, a tablet used for placing orders at a restaurant may also provide suggestions of what to eat.

Another aspect of consumer state is their social state. Social networking may provide a detailed snapshot of the social state of a consumer, from the number of contacts they may have to their depth and variety, and the purchasing habits of the consumer's friends and associates. The social network analysis module 354 may, if provided with access to the consumer's social network through, for example, information provided on a smart card or cell phone, be able to mine her profile and other information to judge her social state. An associated rule set within the rule module 360 may then offer suggestions for purchases or other consumer behavior that is consonant with that social state.

For example, if a consumer utilizes this system in the context of a restaurant offering a large variety of different food types and the consumer, through his social network, is seen to belong to a club devoted to one particular type of food, then the rule set might suggest a food of that type. A paucity of social contact may indicate loneliness, which may be treated by the system as sadness. Social norms of friends may be followed if positive (e.g., "your friend Joe ordered ginger herbal tea instead of coffee, so perhaps you would like it as well") or they may be interpreted as a source of negative peer pressure that the embodiment may help the user resist. (If a consumer trying to improve the state of his health is with friends ordering cheese fries, the system may be relied upon to order on behalf of the consumer based on a predetermined policy favoring more healthful choices.)

The social network analysis module 354 may also be provided with access to the social and/or work calendar of the consumer, wherever such calendar may be kept (e.g., on a smart phone, in the cloud, or integrated into a social network's web site, etc.). However the calendar information is acquired, in one embodiment it may be copied over and stored in database 336 for use by the characterization module 350. Calendar information may provide useful information as to the consumer's emotional state—e.g., a packed calendar may suggest stress—as well as provide contextual information that on its own may be useful for generating suggestions. For example, if the calendar indicates that the consumer is scheduled to catch an early morning flight to attend a business meeting, then an associated rule list may direct the consumer away from purchasing heavily caffeinated beverages, depending on the time of day.

In other embodiments, access to the consumer's calendar may be provided to the self-tracking analysis module 356 or to other modules, as calendar information may be useful to the analysis of these modules as well.

A consumer's financial state is often a major driver of his purchasing decisions. Depending on the depth and range of personal financial information made available to the system, the financial analysis module 357 may determine the consumer's financial state, and an associated rule set within the rule module 360 may then generate suggestions consonant with that financial state. Embodiments may offer multiple levels of analysis, depending on their specific implementation, and there may be substantial interplay among the various analytical modules and rule sets within the SLU 340.

Figure 4:
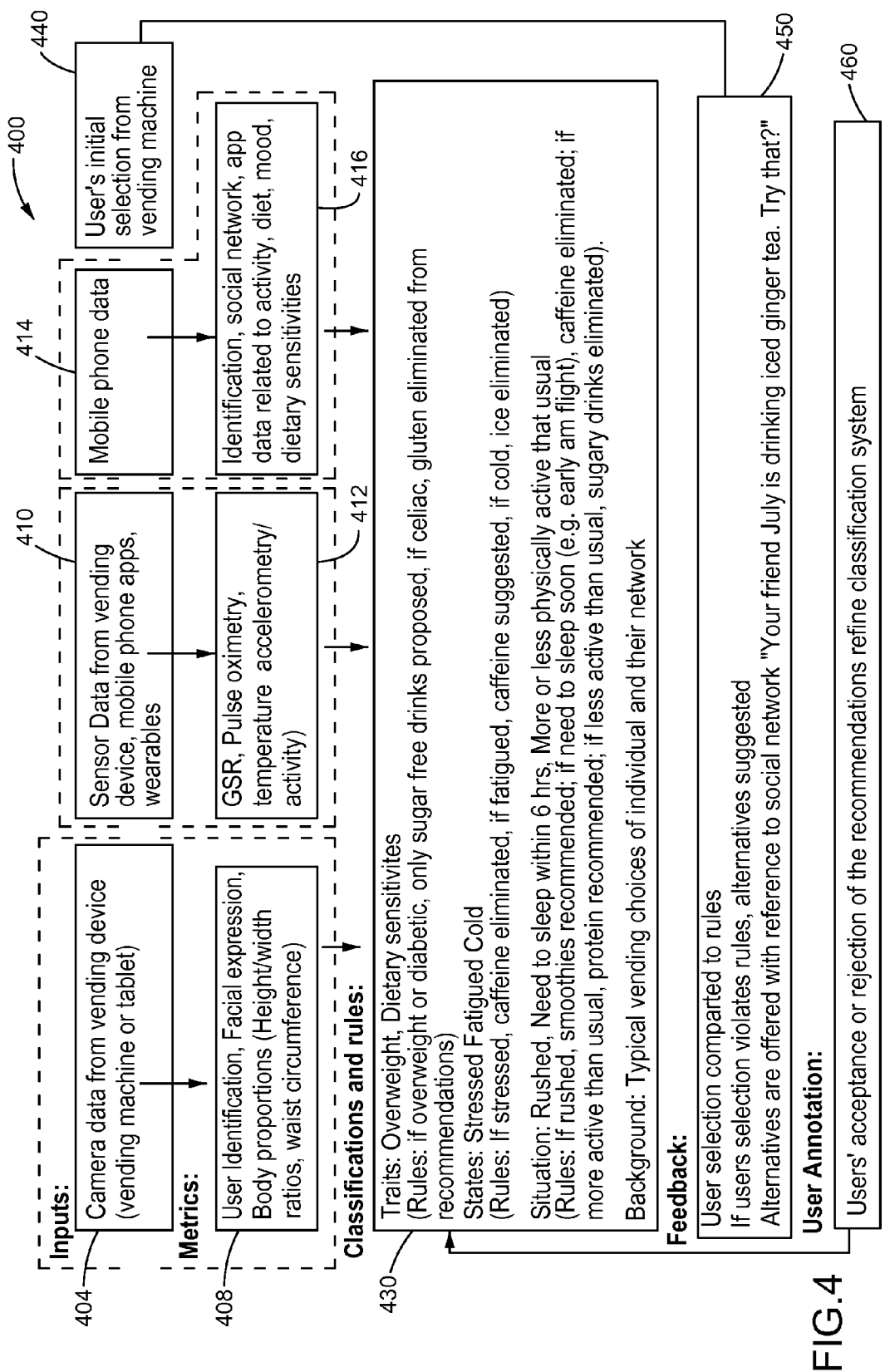
FIG. 4 is a block diagram of an example of a method of utilizing consumer state information according to an embodiment.

FIG. 4 shows a block diagram 400 in which a vending machine suggests drinks based on various sources of data. In this example, the data are grouped by input source. At block 404, image data provided by a camera, which may be integrated into a vending machine (e.g. camera 110 of FIG. 1) or provided through a consumer's tablet or smart phone, may be analyzed at block 408 to characterize the consumer's facial expression (as discussed above) and body proportions (height/width ratios, waist size). Still more data may be provided to the system at block 410 from sensors built into the vending machine (e.g. biometric sensors), or via smart phone apparatus. For example, smart phones may be equipped with an accelerometer, and this may be used to generate data to serve as a marker for the consumer's recent physical activity. Physical activity tracking and mood tracking, whether consumer defined or inferred, may also be gleamed from mobile applications or wearable devices at blocks 410 and 414. Biometric data such as GSR, pulse oximetry, and body temperature may be analyzed at block 412 to further characterize the state of the consumer. At block 414, data accessible via smart phone may provide direct identification of the consumer. The smart phone may also have other applications relating to the consumer's social network, calendar, activity, diet, mood, dietary sensitivities and so forth, as the range of information that may be directly stored on such devices or accessed through them may be comprehensive.

Block 430 presents examples of rule sets and particular suggestions that they may offer. If the consumer is determined to be overweight or to have particular dietary sensitivities, then the system may suggest sugar free drinks. If the consumer suffers from celiac disease, it may suggest choices that are gluten free.

The data gathered may characterize the consumer in other ways. If the consumer is judged to be stressed, as may be inferred from elevated GSR, pulse, facial expression, a mood tracking application or a tightly packed calendar, then suggestions proffered would not include caffeinated beverages. On the other hand, if the consumer is determined to be fatigued according to facial expression, posture, sleep monitoring applications or mood tracking data, then a caffeinated beverage might be suggested. Access to the consumer's calendar may provide information as to how rushed she is and the rules may again take this into consideration.

After being presented with these suggestions, the consumer makes a selection at block 440. The system may then compare the consumer selection to the rule sets and offer an alternative. In most settings, the final decision will be the consumer's to make, notwithstanding the rule sets employed. At block 460, the user's acceptance or rejection of the recommendations is noted and may further be used to further refine the system via this feedback. The system may thus improve on its performance in offering suggestions that the consumer will accept.

In other embodiments, the consumer may agree in advance to hard-code the system so that its rules may not be overridden. Such an arrangement may be of particular value to a dieter trying to lose weight and fearful of the temptations that various venues provide. In this case the consumer's choices would be limited to what is suggested.

Figure 5:
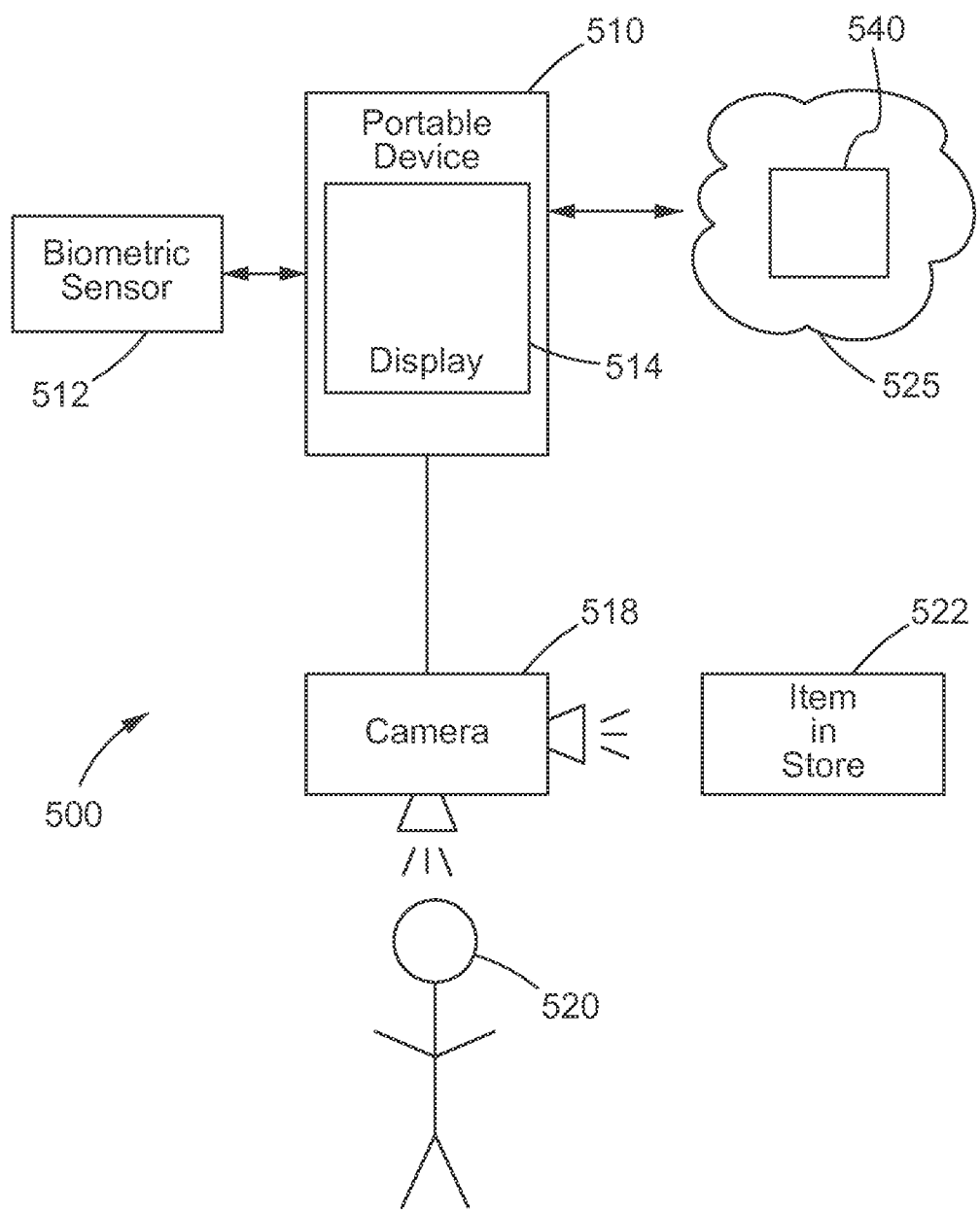
FIG. 5 is a block diagram of an example of a system that uses a portable device according to an embodiment.

FIG. 5 depicts an example of a system 500 that may be used in more general retail settings. The consumer 520 is provided with a portable device 510 such as a smart phone or tablet having a display 514, camera 518 and access to the cloud 525. The portable device may further have a biometric reader 512. Within cloud 525 may be a suggestion logic unit 540 architecturally similar to the SLU 340 discussed above.

Using a self-image taken by the camera 518, data provided by the biometric reader 512, as well as such other information that smart phones and tablets may provide access to, the illustrated SLU 540 determines the consumer's state. If the consumer uses the camera to point to particular merchandise in a store or scans in its bar code, the identity of that merchandise may be conveyed to the system and the SLU 540 may generate suggestions, which may or may not be identical to the merchandise. For example, the rule set may include various fashion rules and these may determine that the consumer is contemplating buying an article of clothing in the wrong size, based on its knowledge of the consumer's size, or that it is too expensive, based on its understanding of the consumer's financial state.

The term "smart" as an adjective before a noun, such as "smart phone" includes devices that have one or more capabilities associated with smart phones, such as geolocation capability, the ability to communicate with another device including the cloud, an interactive display, or other feature. The wearable device may be a so-called smart device, in that it has access to one or more of the capabilities now common with smart phones, including geo-location, access to the internet via Wi-Fi, near field communications, Bluetooth or other communication protocol. Such access may be direct or it may be via a Bluetooth connection with a nearby smart phone or a wearable device worn elsewhere on the consumer's person.

In various embodiments, the interface between consumer and point of sale may be implemented as a wireless system, a wired system, or a combination of both. When implemented as a wireless system, embodiments may include components and interfaces suitable for communicating over a wireless shared media, such as one or more antennas, transmitters, receivers, transceivers, amplifiers, filters, control logic, and so forth. An example of wireless shared media may include portions of a wireless spectrum, such as the radio frequency spectrum and so forth. When implemented as a wired system, embodiments may include components and interfaces suitable for communicating over wired communications media, such as input/output (I/O) adapters, physical connectors to connect the I/O adapter with a corresponding wired communications medium, a network interface card (NIC), disc controller, video controller, audio controller, and so forth. Examples of wired communications media may include a wire, cable, metal leads, printed circuit board (PCB), backplane, switch fabric, semiconductor material, twisted-pair wire, co-axial cable, fiber optics, and so forth.

Embodiments disclosed herein may establish one or more logical or physical channels to communicate information. The information may include media information and control information. Media information may refer to any data representing content meant for a consumer. Examples of content may include, for example, data from a voice conversation, videoconference, streaming video, electronic mail ("email") message, voice mail message, alphanumeric symbols, graphics, image, video, text and so forth. Data from a voice conversation may be, for example, speech information, silence periods, background noise, comfort noise, tones and so forth. Control information may refer to any data representing commands, instructions or control words meant for an automated system. For example, control information may be used to route media information through a system, or instruct a node to process the media information in a predetermined manner.

Additional Notes and Examples

Example 1 may include a system to suggest items to a consumer, comprising a suggestion logic unit that has a state characterization module to characterize a state of a consumer based on data provided by one or more of a reader, a sensor, a portable device, a computer, a database, a microphone or a camera. The suggestion logic unit also has a rule module to generate a set of vending suggestions based on the state of the consumer. A dispenser is present to provide items to the consumer in response to one or more consumer selections from the set of vending suggestions.

Example 2 may include the system of Example 1, wherein the dispenser provides items to the consumer that are restricted to the vending suggestions Example 3 may include the system of Example 1, wherein the state characterization module further comprises one or more of a biometric analysis module, a social network analysis module, a medical records analysis module, a self-tracking analysis module, a body morphology analysis module, or a financial module to characterize a consumer's state.

Example 4 may include the system of claim Example 1, further comprising a vending machine into which the dispenser is integrated.

Example 5 may include the system of Example 1, wherein the rule module comprises a plurality of rule sets.

Example 6 may include the system of Example 1, wherein the system is part of an e-commerce web site.

Example 7 may include any of the systems of any one of Examples 1-4, wherein the state characterization module is to determine the state of one or more of a consumer's physical state, emotional state, social state, or financial state based on said data.

Example 8 may include any of the systems of any one of Examples 1-3, further comprising a data resource to store information regarding a consumer, including data obtained from one or more of a reader, a sensor, a portable device, a database, a computer, or a camera.

Example 9 may include a method to suggest items to be vended to a consumer, comprising receiving data concerning a consumer obtained from one or more of a reader, a sensor, a portable device, a computer, a database, a microphone, or a camera, analyzing the data to characterize a state of the consumer, and using the state of the consumer and at least one rule set to determine a vending suggestion to be offered to the consumer.

Example 10 may include the method of Example 9, wherein the items are merchandise.

Example 11 may include the method of Example 9, further including obtaining image data of the consumer and determining the consumer's emotional state by analyzing the image data.

Example 12 may include the method of Example 9, wherein data based on one or more of a consumer's facial expression, posture, self-characterization of mood, sleep pattern, pulse rate, or galvanic stress response is used to determine an emotional state of the consumer, and wherein vending suggestions are based at least partly on said emotional state.

Example 13 may include the method of either Examples 9 or 12, further including determining the consumer's physical state by analyzing one or more of biometric data or medical records and suggesting items to the consumer based on the physical state of the consumer.

Example 14 may include the method of either Examples 9 or 12, further including determining the consumer's financial state by analyzing financial records of the consumer and suggesting items to the consumer based on the financial state of the consumer.

Example 15 may include the method of Example 9, further including restricting items available to be selected by the consumer to those that are suggested.

Example 16 may include at least one computer readable storage medium comprising a set of instructions which, if executed by a computing device, cause the computing device to receive data concerning a consumer obtained from one or more of a reader, a sensor, a portable device, a computer, a database, a microphone, or a camera, analyze the data to characterize a state of the consumer, and use the state of the consumer and at least one rule set to determine at least one vending suggestion to be offered to the consumer.

Example 17 may include the at least one computer readable storage medium of Example 16, wherein the instructions, if executed, cause a computing device to characterize a consumer's emotional state using data based on one or more of a consumer's facial expression, posture, consumer's self-characterization of mood, sleep pattern, pulse rate, calendar, or galvanic stress response.

Example 18 may include the at least one computer readable storage medium of Example 16, wherein the instructions, if executed, cause a computing device to characterize a consumer's state using data based on the consumer's social network.

Example 19 may include the at least one computer readable storage medium of any one of Examples 16 or 18, wherein the instructions, if executed, cause a computing device to determine the consumer's physical state by analyzing one or more of biometric data or medical records to determine at least one vending suggestion based on the consumer's physical state.

Example 20 may include the at least one computer readable storage medium of Example 16, wherein the instructions, if executed, cause a computing device to determine the consumer's financial state by analyzing financial records of the consumer to determine at least one vending suggestion based on the consumer's financial state.

Example 21 may include an apparatus to vend items, comprising a biosensor to provide biometric data of a consumer, a camera to provide image data of a consumer's face, and a display on which to present suggestions of items to purchase, wherein the suggestions are based on one or more of the biometric data or the image data.

Example 22 may include the apparatus of Example 21, further comprising one or more of a near field communications port, a Wi-Fi port, or a Bluetooth port.

Example 23 may include the apparatus of Example 21, further comprising a dispenser to provide items to the consumer.

Example 24 may include the apparatus of Example 21, further comprising a data processing resource to contain data relating to the state of the consumer.

Example 25 may include the apparatus of any of Examples 21-24, wherein the apparatus comprises a vending machine.

Example 26 may include an apparatus for vending items, comprising means for obtaining biometric data, means for obtaining image data of a consumer's face, and a display on which to present at least one or more suggestions of item to purchase, wherein the suggestions are based on the user's state, which is based on one or more of the biometric data or the image data.

Example 27 may include a system for generating one or more suggestions of expenditures to a consumer, comprising means for determining one or more of the emotional state, financial state, social state, or physical state of a user, and means for determining expenditure suggestions based on a state.

Example 28 may include the system of Example 27, wherein the expenditures are for one or more of merchandise, services, entertainment, food, or drink.

Example 29 may include the system of Examples 27 or 28, further comprising a vending machine to provide items corresponding to the expenditures.

Example 30 may include an apparatus to suggest items for purchase, comprising a characterization module for determining a state of a consumer, wherein the characterization module comprises one or more of a facial analysis module, a body morphology analysis module, a biometric analysis module, a social network analysis module, a medical records analysis module, and a financial analysis module, a rule module comprising at least one rule set to generate a set of vending suggestions based on the state of the consumer, and a consumer interface on which to present the vending suggestions.

Example 31 may include the apparatus of Example 30, wherein information provided by an image of a consumer's face is analyzed by the facial analysis module to determine the consumer's emotional state.

Example 32 may include the apparatus of Example 30, wherein information provided by a biometric reader is analyzed by the biometric analysis module to determine the consumer's health.

Example 33 may include the apparatus of Example 32, wherein the biometric reader provides information about one or more of a consumer's pulse rate, heart rate, blood sugar level, galvanic skin response, blood pressure, or blood oxygen level.

Example 34 may include the apparatus of any of Examples 30-33, comprising means for receiving information from a portable device that may be used to help characterize a consumer's state.

Example 35 may include the apparatus of Example 30, comprising means for determining an emotional state of a consumer based on one or more of biometric data of a consumer, social network, or an image of a consumer's face.

Example 36 may include the apparatus of any of Examples 30-33, comprising a user interface through which the consumer is able to accept, modify, investigate or reject suggestions.

Example 37 may include the apparatus of any of Examples 30-33, comprising means by which the apparatus improves its suggestions by analyzing consumer selections.

Example 38 may include a method to provide suggestions of items to a consumer to purchase, comprising collecting information concerning the consumer from at least one of a database, biometric sensor, or facial image acquired by a camera at a vending machine, analyzing said information to determine at least one of the consumer's emotional or physical state, generating suggestions of items for the consumer to purchase based on a rule set and a consumer state, presenting said suggestions of items to the consumer, and receiving a selection for an item from the consumer.

Example 39 may include the method of Example 38, further comprising providing the consumer with the selected item.

Example 40 may include the method of Example 38, including providing the consumer with the item selected only if it corresponds to a suggested item.

Example 41 may include the methods of any of Examples 38-40, wherein the rule set is to enhance the consumer's physical health.

Example 42 may include the methods of any of Examples 38-40, wherein the rule set is to enhance the consumer's emotional state.

Example 43 may include the method of Example 39, wherein the rule set is to enhance a business's profits.

Example 44 may include the method of Example 38, further comprising means for refining the suggestions based on consumer behavior in accepting or rejecting suggestions.

Example 45 may include the method of Example 38, further including obtaining data about the consumer from a wearable device.

Example 46 may include the method of Example 38, further including obtaining data about the consumer via a cell phone or a tablet.

Example 47 may include the method of Example 38, further including using a consumer's self-characterization to generate suggestions.

Various embodiments may be implemented using hardware elements, software elements, or a combination of both. Examples of hardware elements may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chipsets, and so forth. Examples of software may include software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. Determining whether an embodiment is implemented using hardware elements and/or software elements may vary in accordance with any number of factors, such as desired computational rate, power levels, heat tolerances, processing cycle budget, input data rates, output data rates, memory resources, data bus speeds and other design or performance constraints.

One or more aspects of at least one embodiment may be implemented by representative instructions stored on a machine-readable medium which represents various logic within the processor, which when read by a machine causes the machine to fabricate logic to perform the techniques described herein. Such representations, known as "IP cores" may be stored on a tangible, machine readable medium and supplied to various customers or manufacturing facilities to load into the fabrication machines that actually make the logic or processor.

Further, arrangements may be shown in block diagram form in order to avoid obscuring embodiments, and also in view of the fact that specifics with respect to implementation of such block diagram arrangements are highly dependent upon the platform within which the embodiment is to be implemented, i.e., such specifics should be well within purview of one skilled in the art. Where specific details (e.g., circuits) are set forth in order to describe example embodiments, it should be apparent to one skilled in the art that embodiments may be practiced without, or with variation of, these specific details. The description is thus to be regarded as illustrative instead of limiting.

Those skilled in the art will appreciate from the foregoing description that the broad techniques of the embodiments may be implemented in a variety of forms. Therefore, while the embodiments have been described in connection with particular examples thereof, the true scope of the embodiments should not be so limited since other modifications will become apparent to the skilled practitioner upon a study of the drawings, specification, and following claims.

What is claimed is:

1. A system to suggest items to a consumer, comprising:
a processor;
a suggestion logic unit, implemented by the processor, wherein the suggestion logic unit comprises:
a state characterization logic module configured to characterize a state including an emotional state exclusively of a consumer based on data provided by the consumer to one or more of a reader, a sensor, a portable device, a computer, a database, a microphone or a camera, wherein the characterization of the emotional state is made independently of a history of the consumer, and wherein the state characterization logic module includes:
a social network analysis logic module configured to characterize the state using data based on mining the consumer's social network, and
a facial analysis logic module configured to characterize the state using data based on a facial analysis of the consumer; and
a rule logic module configured to generate a set of vending suggestions independently of the history of the consumer based on the emotional state exclusively of the consumer as characterized by the state characterization logic module;
a display presenting the set of vending suggestions to the consumer; and
an electro-mechanical dispenser to providing items to the consumer in response to one or more consumer selections from the set of vending suggestions presented to the consumer on the display, and wherein the electro-mechanical dispenser provides items to the consumer that are restricted to the vending suggestions.

2. The system of claim 1, wherein the state characterization logic module includes a body morphology analysis module configured to characterize the state using data based on a body morphology analysis of the consumer.

3. The system of claim 1, wherein the state characterization logic module further comprises one or more of a biometric analysis logic module, implemented at least partly in one or more of configurable logic or fixed functionality logic hardware, a medical records analysis logic module, implemented at least partly in one or more of configurable logic or fixed functionality logic hardware, a self-tracking analysis logic module, implemented at least partly in one or more of configurable logic or fixed functionality logic hardware, or a financial analysis logic module, implemented at least partly in one or more of configurable logic or fixed functionality logic hardware, to characterize a consumer's state.

4. The system of claim 1, further comprising a vending machine into which the electro-mechanical dispenser is integrated.

5. The system of claim 1, wherein the rule logic module comprises a plurality of rule sets.

6. The system of claim 1, wherein the system is connected to an e-commerce web site.

7. The system of claim 1, wherein the state characterization logic module is to determine the state of one or more of a consumer's physical state, social state, or financial state based on said data.

8. The system of claim 1, further comprising a data resource to store information regarding a consumer, including data obtained from one or more of a reader, a sensor, a portable device, a database, a computer, or a camera.

9. A method to suggest items to be vended to a consumer at a vending machine, comprising:
receiving, by a processor, data concerning a consumer obtained from one or more of a reader, a sensor, a portable device, a computer, a database, a microphone, or a camera;
analyzing, by the processor, the data at a state characterization logic module;
characterizing, by the processor, an emotional state exclusively of the consumer, wherein the characterization of the emotional state is made independently of a history of the consumer, and wherein the state is based on mining the consumer's social network and on a facial analysis of the consumer;
determining, by the processor, one or more vending suggestions to be offered to the consumer independently of the history of the consumer using the emotional state exclusively of the consumer and at least one rule set;
displaying, by the processor, the one or more vending suggestions to the consumer on a display;
receiving, by the processor, a consumer selection of at least one of the one or more suggested vending items on the display; and
dispensing, by an electro-mechanical dispenser, at least one consumer selected item to the consumer, wherein the electro-mechanical dispenser provides items to the consumer that are restricted to the vending suggestions, wherein data based on one or more of a consumer's facial expression, posture, self-characterization of mood, or sleep pattern is used to determine an emotional state exclusively of the consumer, and wherein the vending suggestion is based at least partly on said emotional state.

10. The method of claim 9, wherein the items are merchandise.

11. The method of claim 9, further including obtaining image data of the consumer independent of the vending suggestion and determining the consumer's emotional state by analyzing the image data.

12. The method of claim 9, wherein data based on one or more of a consumer's pulse rate or galvanic stress response is used to determine the emotional state of the consumer.

13. The method of claim 9, further including determining the consumer's physical state by analyzing one or more of biometric data, body shape, or medical records and suggesting items to the consumer based on the physical state of the consumer.

14. The method of claim 9, further including determining the consumer's financial state by analyzing financial records of the consumer and suggesting items to the consumer based on the financial state of the consumer.

15. The method of claim 9, further including characterizing the state using data based on a body morphology analysis of the consumer.

16. At least one non-transitory computer readable storage medium comprising a set of instructions that when executed by a computing device, cause the computing device to:
receive data concerning a consumer obtained from one or more of a reader, a sensor, a portable device, a computer, a database, a microphone, or a camera;
analyze the data at a state characterization logic module;
characterize an emotional state exclusively of the consumer, wherein the characterization of the emotional state is made independently of a history of the consumer, and wherein the state is based on mining the consumer's social network and on a facial analysis of the consumer;

determine one or more vending suggestions to be offered to the consumer independently of the history of the consumer at a vending machine based on at least one rule set and on the emotional state exclusively of the consumer;

present at least one of the one or more vending suggestions to the consumer on a display;

receive a consumer selection of at least one item of the one or more vending suggestions on the display; and dispense, by an electro-mechanical dispenser, the at least one consumer selected item, wherein the electro-mechanical dispenser provides items to the consumer that are restricted to the vending suggestions, wherein the consumer's emotional state is characterized using data based on one or more of a consumer's facial expression, posture, consumer's self-characterization of mood, sleep pattern, or calendar.

17. The at least one non-transitory computer readable storage medium of claim 16, wherein the instructions, when executed, cause a computing device to characterize the consumer's emotional state using data based on one or more of a consumer's pulse rate or galvanic stress response.

18. The at least on non-transitory computer readable storage medium of claim 16, wherein the instructions, when executed, cause a computing device to characterize the consumer's state using data based on a body morphology analysis of the consumer.

19. The at least one non-transitory computer readable storage medium of claim 16, wherein the instructions, when executed, cause a computing device to determine the consumer's physical state by analyzing one or more of biometric data or medical records to determine at least one vending suggestion based on the consumer's physical state.

20. The at least one non-transitory computer readable storage medium of claim 16, wherein the instructions, when executed, cause a computing device to determine the consumer's financial state by analyzing financial records of the consumer to determine at least one vending suggestion based on the consumer's financial state.

21. An apparatus to vend items, comprising:
a processor;
a biometric sensor providing biometric data exclusively of a consumer;
a camera providing image data exclusively of the consumer of one or more of the consumer's facial expression, body proportions, or posture;
a suggestion logic unit, implemented by the processor, wherein the suggestion logic unit comprises:
  a state characterization logic module configured to characterize a state including an emotional state exclusively of a consumer based on data provided by the consumer to one or more of a reader, a sensor, a portable device, a computer, a database, a microphone or a camera, wherein the characterization of the emotional state is made independently of a history of the consumer, and wherein the state characterization logic module includes: a social network analysis logic module configured to characterize the state using data based on mining the consumer's social network, and a facial analysis logic module configured to characterize the state using data based on a facial analysis of the consumer; and
  a rule logic module configured to generate a set of vending suggestions independently of the history of the consumer based on the emotional state exclusively of the consumer as characterized by the state characterization logic module;
a display presenting the set of vending suggestions to the consumer; and
an electro-mechanical dispenser providing items to the consumer in response to one or more consumer selections from the set of vending suggestions presented to the consumer on the display, wherein the electro-mechanical dispenser provides items to the consumer that are restricted to the vending suggestions.

22. The apparatus of claim 21, further comprising one or more of a near field communications port, a Wi-Fi port, or a wireless personal area network port.

23. The apparatus of claim 21, further comprising a data processing resource to contain data relating to the state of the consumer.

24. The apparatus of claim 21, wherein the apparatus comprises a vending machine.

25. The apparatus of claim 21, wherein the state characterization logic module includes a body morphology analysis module configured to characterize the state using data based on a body morphology analysis of the consumer.

* * * * *